United States Patent
Norisue et al.

(10) Patent No.: US 6,677,475 B2
(45) Date of Patent: Jan. 13, 2004

(54) OPTICALLY ACTIVE COMPOUND AND LIQUID CRYSTAL COMPOSITION CONTAINING THE COMPOUND

(75) Inventors: Yasumasa Norisue, Katsushika-ku (JP); Takakiyo Mine, Katsushika-ku (JP); Masahiro Johno, Katsushika-ku (JP)

(73) Assignee: Mitsubishi Gas Chemical Co., Inc., Tokyo (JP)

( * ) Notice: Subject to any disclaimer, the term of this patent is extended or adjusted under 35 U.S.C. 154(b) by 44 days.

(21) Appl. No.: 10/046,902

(22) Filed: Jan. 17, 2002

(65) Prior Publication Data

US 2002/0146517 A1 Oct. 10, 2002

(30) Foreign Application Priority Data

Jan. 22, 2001 (JP) ......................... 2001-013247
May 23, 2001 (JP) ......................... 2001-153467
May 23, 2001 (JP) ......................... 2001-153468

(51) Int. Cl.$^7$ .................. C07C 69/76; C07C 25/13; C09K 19/12; C09K 19/30
(52) U.S. Cl. ..................... 560/59; 560/65; 560/85; 570/129; 570/130; 252/299.63; 252/299.64; 252/299.65
(58) Field of Search ................. 428/1.1; 252/299.01, 252/299.64, 299.63, 299.65; 560/59, 65; 570/129, 130

(56) References Cited

U.S. PATENT DOCUMENTS

| | | | |
|---|---|---|---|
| 4,968,820 A | | 11/1990 | Scherowsky et al. |
| 4,996,330 A | | 2/1991 | Scherowsky et al. |
| 5,972,243 A | * | 10/1999 | Mine et al. ............ 252/299.65 |
| 6,133,469 A | * | 10/2000 | Mine et al. ................ 560/59 |
| 6,217,792 B1 | | 4/2001 | Parri et al. ............. 252/299.61 |
| 6,338,883 B1 | | 1/2002 | Iwamatsu et al. |
| 6,372,308 B1 | * | 4/2002 | Yoshioka et al. ........... 428/1.1 |

FOREIGN PATENT DOCUMENTS

| | | | |
|---|---|---|---|
| EP | 0-233602 A2 | 8/1987 | ........... C07C/69/75 |
| EP | 0-517504 A1 | 12/1992 | |
| EP | 0-528268 A2 | 2/1993 | |
| GB | 2-348883 A | 10/2000 | |
| JP | 62-195347 | 8/1987 | ........... C07C/69/75 |
| JP | 02-053768 | 2/1990 | ....... C07D/207/416 |
| JP | 2000-178557 | 6/2000 | |
| WO | WO 98/00428 | 1/1998 | |

OTHER PUBLICATIONS

Murashiro, K. et al., Dopant Effect On Threshold Electric Field Of Antiferroelectric Liquid Crystal Switching, Lquid Crystals, Taylor and Francis LTD, London, GB, vol. 14, No. 2, pp. 371–380 (1993).

* cited by examiner

Primary Examiner—Shean C. Wu
(74) Attorney, Agent, or Firm—Sherman & Shalloway (57) ABSTRACT

Optically active compounds of the following general formula (1) useful as chiral dopant,

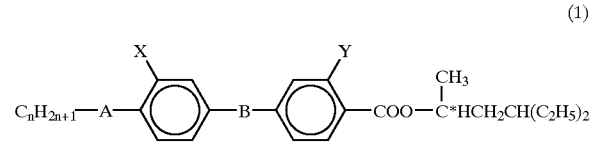

(1)

wherein n is an integer of 0 to 5, provided that when n is 0, A is a single bond (—) and that when n is 1 to 5, A is a single bond (—), —O—, —COO—, —Cy— or —Cy—COO— in which —Cy— is a trans-1,4-cyclohexylene group, each of X and Y is independently a hydrogen atom or a fluorine atom, B is a single bond (—), —COO—, —COO—Ph— or —Ph—COO— in which —Ph— is a 1,4-phenylene group, and C* is an asymmetric carbon. The chiral dopant of the present invention have a high helical twisting power of at least 9 and suitably have a feature that the helical pitch induced by them decreases in length with an increase in temperature so that they are advantageous for use in a nematic liquid crystal composition.

10 Claims, 1 Drawing Sheet

OPTICALLY ACTIVE COMPOUND AND LIQUID CRYSTAL COMPOSITION CONTAINING THE COMPOUND

DETAILED DESCRIPTION OF THE INVENTION

1. Field of the Invention

The present invention relates to a novel optically active compound, useful as chiral dopant, a nematic liquid crystal composition containing such a compound and a liquid crystal display device having the liquid crystal composition interposed between transparent electrodes. More specifically, it relates to a chiral dopant having a helical twisting power (HTP) of at least 9 and having properties of induced helical pitch decreasing with an increase in temperature and a use thereof.

2. Prior Art

Various modes are known as display modes of liquid crystal display devices, and in most display modes, it is required to control the helical pitch of a liquid crystal. The mode that requires control of the helical pitch of a liquid crystal includes the following modes.

The modes that have been put to practical use and often employed are a twisted nematic mode (TN mode) and a super twisted nematic mode (STN mode) using a nematic liquid crystal.

In the TN mode, liquid crystal molecules are aligned so as to twist at 90 degrees between an upper substrate and a lower substrate, and a ¼ pitch of a helix is formed in a cell.

In the STN mode, liquid crystal molecules are aligned so as to twist at approximately 220 degrees between an upper substrate and a lower substrate, and a ⅗ pitch of a helix is formed in a cell.

The TN mode is employed in a simple matrix driving liquid crystal display device and an active matrix driving liquid crystal display device, and the STN mode is employed in a simple matrix driving liquid crystal display device.

Figure 1:
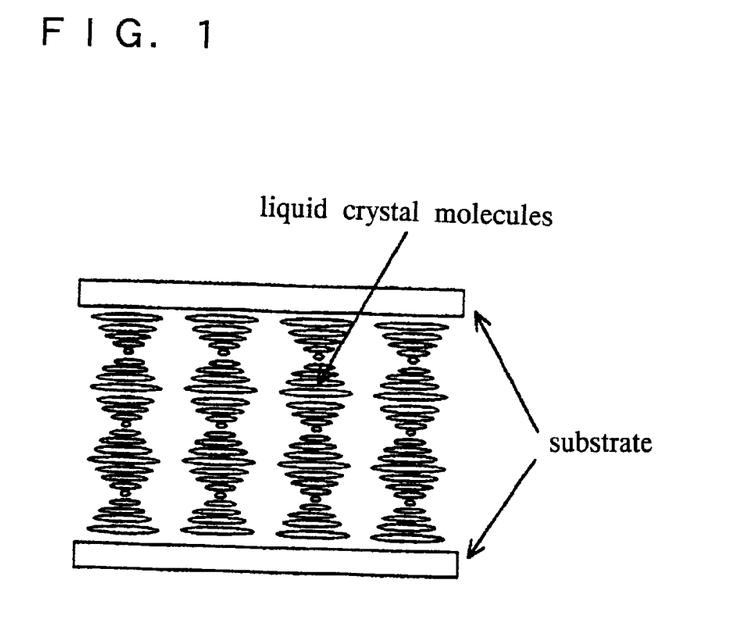
FIG. 1 is a schematic showing of a planar alignment of a chiral nematic liquid crystal.
Figure 2:
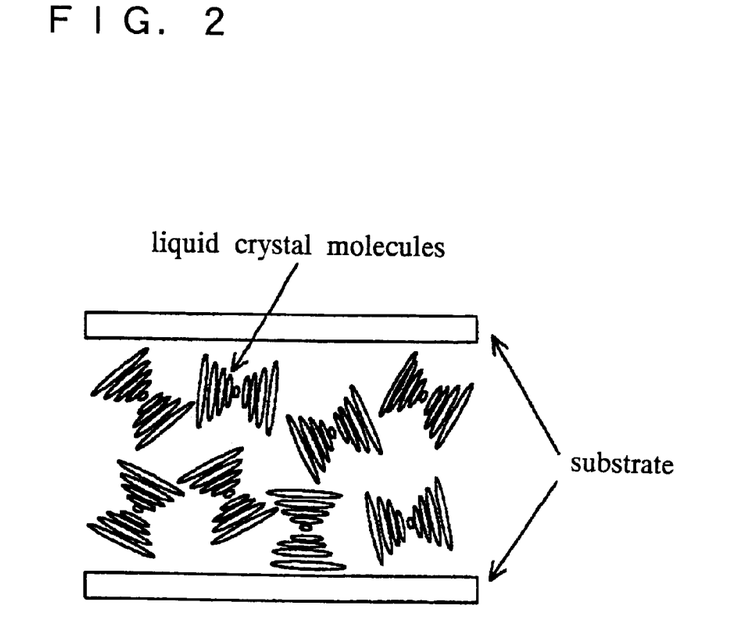
FIG. 2 is a schematic showing of a focal-conic alignment of a chiral nematic liquid crystal.

As another mode in addition to the above TN mode and STN mode, there is a selective reflection (SR) mode of a chiral nematic liquid crystal. As shown in FIGS. 1 and 2, in the SR mode, a liquid crystal has a planar alignment state (FIG. 1) in which helical axes are perpendicular to substrates and a focal-conic alignment state (FIG. 2) in which directions of helical axes are at random. These two states are switched with voltage pulse. In the planar alignment state, light having a wavelength corresponding to a helical pitch is reflected, and in the focal-conic alignment state, light is transmitted through a device. When a reflection state is used as "bright" and when a transmission state is used as "dark", a display is made possible.

In the present invention, the term "nematic liquid crystal" means a nematic liquid crystal containing no chiral dopant of the present invention. Further, the term "liquid crystal composition" or "nematic liquid crystal composition" means a nematic liquid crystal composition containing a chiral dopant of the present invention. Further, the term "liquid crystal" means a composition containing a plurality of liquid crystal compounds unless otherwise specified. The present invention sometimes refers to "liquid crystal" as "base liquid crystal". Moreover, the term "chiral dopant" means an optically active compound that induces a helical structure or a mixture of such compounds.

An optically active compound that induces a helical structure is generally called a chiral dopant. A number of chiral dopant compounds have been already synthesized, and typical compounds thereof have the following structural formulae.

| Name | Structural formula |
| --- | --- |
| S811: | $C_6H_{13}O$—⟨ ⟩—COO—⟨ ⟩—COOC*HC$_6$H$_{13}$ with CH$_3$ branch |
| CB15: | NC—⟨ ⟩—⟨ ⟩—CH$_2$C*HC$_2$H$_5$ with CH$_3$ branch |
| CN: | $C_8H_{17}$COO— cholesterol structure |

The most essential performance that is required of a chiral dopant compound is to have great helical twisting power. The helical twisting power (HTP) refers to a physical quantity defined by the following expression.

$$HTP(\mu m^{-1}) = 1/(\text{amount of chiral dopant added (wt \%)}/100 \times \text{induced helical pitch } (\mu m))$$

Generally chiral dopants themselves exhibit no liquid crystallinity, and most of them have large molecular weights. When a large amount of a chiral dopant is added to a base liquid crystal, it degrades various performances in many cases. The degradation of the performances includes a decrease in phase transition temperature from an isotropic phase to a nematic phase, an increase in viscosity of a liquid crystal composition and an easy occurrence of crystallization. A chiral dopant having great helical twisting power serves to prevent the degradation of the performances since a desired helical pitch can be obtained by adding a small amount to such a chiral dopant to the base liquid crystal. The base liquid crystal refers to a liquid crystal to which a chiral dopant is added.

In addition to the above problems, the SR mode further has a problem that the helical pitch depends upon temperatures. That is, in the SR mode, a liquid crystal reflects (selectively reflects) light corresponding to a helical pitch to produce a bright state. However, when chiral dopants that have been already developed are used, the helical pitch increases in length with an increase in temperature, so that there is caused a problem that reflected light comes to change in color.

A change in wavelength of selectively reflected light with an increase in temperature is referred to as "wavelength shift". An increase in wavelength of selectively reflected light due to an increase in temperature is defined to be plus wavelength shift, and a decrease in wavelength of selectively reflected light due to an increase in temperature is defined to be minus wavelength shift.

For removing the dependency of wavelength of selectively reflected light upon temperatures, studies have been made on combinations of a chiral dopant that shows a plus wavelength shift and a chiral dopant that shows a minus wavelength shift.

However, there are very few chiral dopants that show a minus wavelength shift, and there are only four chiral dopants having a helical twisting power (HTP) of at least 9, which are disclosed in U.S. Pat. No. 6217792, JP-A-62-195347 and JP-A-2-053768. Those compounds that have been so far disclosed are not satisfactory, since these compounds exhibit small shift amounts and have a problem that they are liable to cause crystallization even when added in a small amount.

PROBLEMS TO BE SOLVED BY THE INVENTION

It is an object of the present invention to provide a chiral dopant that has great helical twisting power (HTP) and has a characteristic feature that the helical pitch induced decreases in length with an increase in temperature (has a minus wavelength shift).

MEANS TO SOLVE THE PROBLEMS

According to the present invention, there are provided optically active compounds useful as chiral dopant of the following general formula (1).

(1)

wherein n is an integer of 0 to 5, provided that when n is 0, A is a single bond (—) and that when n is 1 to 5, A is a single bond (—), —O—, —COO—, —Cy— or —Cy— COO— in which —Cy— is a trans-1,4-cyclohexylene group, each of X and Y is independently a hydrogen atom or a fluorine atom, B is a single bond (—), —COO—, —COO—Ph— or —Ph—COO— in which —Ph— is a 1,4-phenylene group, and C* is an asymmetric carbon.

In the present invention, preferred are the following compounds (1) to (7) among the compounds of the above general formula (1).

(1) A compound of the general formula (1) in which n is 3.

(2) A compound of the general formula (1) in which X and Y are hydrogen atoms.

(3) A compound of the general formula (1) in which A is a single bond (—) and B is —COO—Ph— or —Ph—COO—.

(4) A compound of the general formula (1) in which n is 3, X and Y are hydrogen atoms, A is a single bond (—) and B is —COO—Ph— or —Ph—COO—.

(5) A compound of the general formula (1) in which B is a single bond (—) and A is a single bond (—), —O—, —COO— or —Cy—COO—.

(6) A compound of the general formula (1) in which n is 3, X and Y are hydrogen atoms, A is —Cy—COO—, and B is a single bond (—).

(7) A compound of the general formula (1) in which B is —COO— and A is —O—, —COO— or —Cy—.

Of the optically active compounds of the present invention, the following compounds are the most preferred for useful as chiral dopant.

Desirably, the optically active compound of the present invention has a helical twisting power (HTP) of at least 9, and more desirably, it has a characteristic feature that the helical pitch induced decreases in length with an increase in temperature (has a minus wavelength shift). Further, the absolute value of the wavelength shift is desirably at least 50 nm, and more desirably at least 100 nm. The compound of the present invention is therefore suitably used as an additive (chiral dopant) to a nematic liquid crystal, and at least one of the optically active compounds of the above general formula (1) is mixed with a nematic liquid crystal and gives a nematic liquid crystal composition. The thus-obtained nematic liquid crystal composition is used in a liquid crystal display device having the above nematic liquid crystal composition interposed between substrates having electrodes.

The optically active compound includes an R-configuration compound and an S-configuration compound, and both compounds can be suitably used. That is, the R-configuration compound and the S-configuration compound differs in properties that induced helical pitches differ in twisted direction (right-twisted or left-twisted). When used, one of these compounds is selected by taking account of the twisting directions of the chiral dopants.

Further, when a large amount of the optically active compound of the present invention alone is added to a nematic liquid crystal as a base liquid crystal to prepare a composition, the composition containing some combination of the nematic liquid crystal with the optically active compound of the present invention sometimes undergoes crystallization in some cases. In such cases, generally, the crystallization can be easily avoided by using other chiral dopant in combination or by replacing the chiral dopant as a main component with other chiral dopant.

When the optically active compound of the present invention is used as a chiral dopant, the amount of the above optically active compound based on the nematic liquid crystal composition containing the chiral dopant is generally 1 to 40% by weight, preferably 1 to 30% by weight. The amount of the optically active compound is preferably determined depending upon a value of helical twisting power of the optically active compound, crystallizability and a type of a nematic liquid crystal compound.

According to the present invention, there is provided a chiral dopant having great helical twisting power and having a characteristic feature that the induced helical pitch decreases in length with an increase in temperature. In liquid crystal compositions for use in the TN mode and the STN mode, therefore, the helical pitch can be adjusted by adding a small amount of the chiral dopant of the present invention, so that the degradation of performances of a base liquid crystal can be prevented. In a liquid crystal composition for use in the SR mode, a chiral dopant for inducing a plus wavelength shift and the chiral dopant of the present invention are used in combination, whereby there can be obtained a liquid crystal composition of which the helical pitch does not change depending upon temperatures.

EXAMPLE

The present invention will be explained further in detail with reference to Examples and Comparative Examples hereinafter, while the present invention shall not be limited thereto.

Example 1

(Formula (1): n=3, A=--, X=H, Y=H, B=—COO—Ph— (E1))

Preparation of (R)-3-ethyl-1-methylpentyl-4'-(4-propylbenzoyloxy)-biphenyl-4-carboxylate (1) Synthesis of 4'-acetoxybiphenyl-4-carboxylic acid 50 Grams (234 mmol) of 4'-hydroxybiphenyl-4-carboxylic acid and 238 g (2.34 mol) of acetic anhydride were placed in a reactor, and 0.1 g of concentrated sulfuric acid was added with stirring. The stirring was continued until heat generation terminated, and further, the reaction mixture was stirred under heat at 80° C. for 4 hours and then cooled to room temperature.

While the reaction mixture was cooled in an ice bath, 500 g of water was gradually added, and the mixture was stirred at room temperature for 3 hours to deactivate unreacted acetic anhydride.

A precipitated white solid was recovered by filtration and washed with water to remove acetic acid, and the solid was dried with a vacuum dryer to give 59.8 g of 4'-acetoxybiphenyl-4-carboxylic acid (yield 99%).

(2) Synthesis of 4'-acetoxybiphenyl-4-carbonyl chloride 59.8 Grams (233.4 mmol) of 4'-acetoxybiphenyl-4-carboxylic acid and 278 g (2.33 mol) of purified thionyl chloride were placed in a reactor and refluxed under heat (79° C.) for 4 hours.

Then, thionyl chloride was distilled off under atmospheric pressure, and 150 ml (milliliters) of toluene was added to the residue. Toluene and thionyl chloride were distilled off under reduced pressure, to give 63 g of 4'-acetoxybiphenyl-4-carbonyl chloride (yield 98%).

(3) Synthesis of (R)-3-ethyl-1-methylpentyl-4'-acetoxybiphenyl-4-carboxylate 18.6 Grams (67.6 mmol) of 4'-acetoxybiphenyl-4-carbonyl chloride, 8.0 g (61.4 mmol) of (R)-4-ethyl-2-hexanol and 140 ml of toluene were placed in a reactor, 9.7 g (122.9 mmol) of pyridine was dropwise added thereto, and the mixture was stirred at room temperature for 3 hours.

To the reaction mixture was added 40 ml of water, and the mixture was stirred at room temperature for 30 minutes. Then, a liquid of an organic layer was separated. The organic layer was washed with 2N hydrochloric acid, with a 1N sodium hydroxide aqueous solution and with water, dried over anhydrous sodium sulfate and filtered, and then the solvent was distilled off to give 22 g of (R)-3-ethyl-1-methylpentyl-4'-acetoxybiphenyl-4-carboxylate (yield 99%).

(4) Synthesis of (R)-3-ethyl-1-methylpentyl-4'-hydroxybiphenyl-4-carboxylate

22 Grams (59.7 mmol) of (R)-3-ethyl-1-methylpentyl-4'-acetoxybiphenyl-4-carboxylate and 390 ml of toluene were placed in a reactor, a methanol solution having a methylamine concentration of 40% was dropwise added thereto, and the mixture was stirred at room temperature for 3 hours.

The reaction mixture was washed and liquid-separated with 2N hydrochloric acid and water, and an organic layer was dried over anhydrous sodium sulfate and filtered. The solvent was distilled off to give 19 g of (R)-3-ethyl-1-methylpentyl-4'-hydroxybiphenyl-4-carboxylate (yield 97%).

(5) Synthesis of (R)-3-ethyl-1-methylpentyl-4'-(4-propylbenzoyloxy)-biphenyl-4-carboxylate 1.2 Grams (6.41 mmol) of p-n-proylbenzoic acid chloride, 1.9 g (5.82 mmol) of (R)-3-ethyl-1-methylpentyl-4'-hydroxybiphenyl-4-carboxylate and 30 ml of toluene were placed in a reactor, 0.9 g (11.6 mmol) of pyridine was dropwise added, and the mixture was stirred at room temperature for 3 hours. After completion of the reaction, water was added, and the mixture was stirred for 30 minutes. A liquid of an organic layer was separated, and consecutively washed with 2N hydrochloric acid, with a 1N sodium hydroxide aqueous solution and with water. The organic layer was dried over anhydrous sodium sulfate and filtered, and the solvent was distilled off, to give 2.6 g of crude (R)-3-ethyl-1-methylpentyl-4'-(4-propylbenzoyloxy)-biphenyl-4-carboxylate (yield 95%).

The thus-obtained crude product was purified with a liquid chromatograph (HPLC) to give 2.3 g of (R)-3-ethyl-1-methylpentyl-4'-(4-propylbenzoyloxy)-biphenyl-4-carboxylate as an end product (yield 84%).

Examples 2–5

(Formula (1): n=1, A=--, X=H, Y=H, B=—COO—Ph— (E2)), Preparation of (R)-3-ethyl-1-methylpentyl-4'-(4-methylbenzoyloxy)-biphenyl-4-carboxylate, (Formula (1): n=2, A=--, X=H, Y=H, B=—COO—Ph— (E3)), Preparation of (R)-3-ethyl-1-methylpentyl-4'-(4-ethylbenzoyloxy)-biphenyl-4-carboxylate, (Formula (1): n=4, A=--, X=H, Y=H, B=—COO—Ph— (E4)), Preparation of (R)-3-ethyl-1-methylpentyl-4'-(4-butylbenzoyloxy)-biphenyl-4-carboxylate, and (Formula (1): n=5, A=--, X=H, Y=H, B=—COO—Ph— (E5)), Preparation of (R)-3-ethyl-1-methylpentyl-4'-(4-pentylbenzoyloxy)-biphenyl-4-carboxylate Each Synthesis was carried out in the same manner as in Example 1 except that the p-n-propylbenzoic acid chloride in Example 1(5) was replaced with p-n-methylbenzoic acid chloride (E2), p-n-ethylbenzoic acid chloride (E3), p-n-butylbenzoic acid chloride (E4) or p-n-pentylbenzoic acid chloride (E5).

Example 6
(Formula (1): n=3, A=—COO—, X=H, Y=H, B=—COO—Ph— (E6)), Preparation of (R)-3-ethyl-1-methylpentyl-4'-(4-butanoyloxybenzoyloxy)-biphenyl-4-carboxylate Preparation was carried out in the same manner as in Example 1 except that the p-n-propylbenzoic acid chloride in Example 1(5) was replaced with 4-butanoyloxybenzoic acid chloride.

Example 7
(Formula (1): n=3, A=—O—, X=H, Y=H, B=—COO—Ph— (E7)), Preparation of (R)-3-ethyl-1-methylpentyl-4'-(4-propyloxybenzoyloxy)-biphenyl-4-carboxylate

Preparation was carried out in the same manner as in Example 1 except that the p-n-propylbenzoic acid chloride in Example 1(5) was replaced with 4-propyloxybenzoic acid chloride.

Example 8
(Formula (1): n=1, A=—, X=F, Y=H, B=—COO—Ph— (E8)), Preparation of (R)-3-ethyl-1-methylpentyl-4'-(3-fluoro-4-methylbenzoyloxy)-biphenyl-4-carboxylate Preparation was carried out in the same manner as in Example 1 except that the p-n-propylbenzoic acid chloride in Example 1(5) was replaced with 3-fluoro-4-methylbenzoic acid chloride.

The optically active compounds (E1 to E8) obtained in the above Examples 1 to 8 were subjected to $^1$H-NMR measurement. Table 1 shows the results corresponding to common portions represented by the general formula, and the following formula (I) shows the structural formula thereof. Table 2 shows the results from portions specific to the compounds together with their structural formula portions.

Further, the compounds (E1 to E8) were evaluated for phase transition temperatures by observation through a polarizing microscope and DSC measurement. The DSC measurement was carried out at a temperature decrease rate of 5° C./minute. Table 3 shows the results.

(I)

TABLE 2

| | Leftmost alkyl chain | | B portion (common to compounds (E1) to (E8)) | | | |
|---|---|---|---|---|---|---|
| Compound | Methyl | Methylene | —COO—Ph— (from COO side) | | | |
| E1 | 0.8–1.0 | 2.70 | 7.31 | 7.67 | 7.31 | 7.67 |
| E2 | 2.47 | — | 7.32 | 7.66 | 7.32 | 7.66 |
| E3 | 0.8–1.0 | 2.76 | 7.33 | 7.66 | 7.33 | 7.66 |
| E4 | 0.8–1.0 | 2.72 | 7.31 | 7.66 | 7.31 | 7.66 |
| E5 | 0.8–1.0 | 2.71 | 7.28 | 7.67 | 7.28 | 7.67 |
| E6 | 1.07 | 2.59 | 7.27 | 7.67 | 7.27 | 7.67 |
| E7 | 1.07 | 4.02 | 7.30 | 7.66 | 7.30 | 7.66 |
| E8 | 2.39 | — | 7.25 | 7.67 | 7.25 | 7.67 |

TABLE 3

| No. | Compound | Phase sequence |
|---|---|---|
| Ex.1 | E 1 | Iso(90)SA(59)Cry |
| Ex.2 | E 2 | Iso(108)Cry |
| Ex.3 | E 3 | Iso(93)Cry |
| Ex.4 | E 4 | Iso(79)SA(57)Cry |
| Ex.5 | E 5 | Iso(87)SA(24)Cry |
| Ex.6 | E 6 | Iso(135)Cry |
| Ex.7 | E 7 | Iso(123)SA(88)Cr |
| Ex.8 | E 8 | Iso(105)Cry |

Ex.: Example
Notes to Table: Parenthesized values show phase transition temperatures (° C.), Iso stands for an isotorpic phase, SA stands for a smectic A phase, and Cry stands for a crystal phase.

Examples 9–16

The optically active compounds (E1 to E8) obtained in the above Examples 1 to 8 were measured for a helical twisting power (HTP) and a wavelength shift.

To a nematic liquid crystal (ZLI-1565) supplied by Merck & Co., Inc., was added 15% by weight of the optically active compound (E1) obtained in Example 1 based on the liquid crystal composition, to prepare a chiral nematic (N*) liquid crystal composition.

The thus-prepared liquid crystal composition was measured for an upper limit temperature of its N* phase and characteristic reflection behaviors, and its helical twisting power (HTP) was determined on the basis of the characteristic reflection behaviors.

The upper-limit temperature of the N* phase was determined by observation through a polarizing microscope and DSC measurement.

The characteristic reflection behaviors were measured according to the following procedures.

TABLE 1

| | Left phenylene group | | | | Right phenylene group | | | | Rightmost alkyl chain | |
|---|---|---|---|---|---|---|---|---|---|---|
| Compound | 1 | 2 | 3 | 4 | 5 | 6 | 7 | 8 | 9 | 10 |
| E1 | 7.31 | 8.10 | 7.31 | 8.10 | 7.67 | 8.10 | 7.67 | 8.10 | 5.26 | 0.88 |
| E2 | 7.32 | 8.12 | 7.32 | 8.12 | 7.66 | 8.12 | 7.66 | 8.12 | 5.26 | 0.88 |
| E3 | 7.33 | 8.12 | 7.33 | 8.12 | 7.66 | 8.12 | 7.66 | 8.12 | 5.26 | 0.88 |
| E4 | 7.31 | 8.12 | 7.31 | 8.12 | 7.66 | 8.12 | 7.66 | 8.12 | 5.26 | 0.88 |
| E5 | 7.28 | 8.12 | 7.28 | 8.12 | 7.67 | 8.12 | 7.67 | 8.12 | 5.27 | 0.88 |
| E6 | 7.27 | 8.12 | 7.27 | 8.12 | 7.67 | 8.25 | 7.67 | 8.25 | 5.26 | 0.87 |
| E7 | 7.66 | 8.15 | 7.66 | 8.15 | 7.66 | 8.15 | 7.66 | 8.15 | 5.27 | 0.88 |
| E8 | — | 7.91 | 7.25 | 7.86 | 7.67 | 8.11 | 7.67 | 8.11 | 5.26 | 0.88 |

A liquid crystal cell with ITO electrodes (cell thickness 10 μm) was charged with the above liquid crystal composition in an isotropic state. The cell was adjusted to 60° C., a rectangular wave voltage of ±60 V was applied for approximately 1 minute, and the cell was rapidly cooled to room temperature to attain planar alignment.

The above liquid crystal cell was evaluated for characteristic reflection behaviors at 25° C. and 60° C. with an automatic spectrophotometer. The helical twisting powers (HTP) at 25° C. and 60° C. were calculated on the basis of the following expressions.

$$HTP(\mu m^{-1}) = n/(\lambda_{25} \times C/100)$$

$$HTP(\mu m^{-1}) = n/(\lambda_{60} \times C/100)$$

wherein n is a refractive index of the chiral nematic liquid crystal, $\lambda_{25}$ is a characteristic reflection wavelength (μm) at 25° C., $\lambda_{60}$ is a characteristic reflection wavelength (μm) at 60° C. and C is a concentration (wt %) of the chiral dopant. The refractive index n refers to a value of 1.6 that is the refractive index of the base liquid crystal ZLI-1565.

The wavelength shift was determined on the basis of the following expression.

$$\text{Wavelength shift (nm)} = \lambda_{60}^* - \lambda_{25}^*$$

wherein $\lambda_{60}^*$ is a characteristic reflection wavelength (μm) at 60° C. and $\lambda_{25}^*$ is a characteristic reflection wavelength (nm) at 25° C.

Table 4 summarizes the results.

It is seen that the optically active compound (E1) in Example 1 has an HTP of more than 9 and further has properties that the helix decreases in length with an increase in temperature.

The optically active compounds (E2 to E8) obtained in Examples 2 to 8 were measured to determine a helical twisting power (HTP) and a wavelength shift in the same manner as above.

In the above measurement, since the liquid crystal composition containing the optically active compound (E6) was partly crystallized at room temperature, an HTP(*) at 40° C. and a wavelength shift(*) between a wavelength at 40° C. and a wavelength at 60° C. were determined, and Table 4 shows such data.

Comparative Examples 1–3

Known optically active compounds CB15, S811 and CN shown in the explanation of Prior Art were measured to determine an HTP and a wavelength shift each in the same manner as in Example 9.

Since CN had a low helical twisting power (HTP), 30% by weight of CN was added to a nematic liquid crystal compound (ZLI-1565) to prepare a liquid crystal composition, and the liquid crystal composition was measured. Table 4 shows such data.

TABLE 4

| No. | Added Compound Name | Iso-N*(° C.) | HTP (1/μm) | Wavelength shift (nm) |
|---|---|---|---|---|
| Ex.9 | E 1 | 85 | 10.5 | −172 |
| Ex.10 | E 2 | 85 | 10.9 | −132 |
| Ex.11 | E 3 | 84 | 10.9 | −168 |
| Ex.12 | E 4 | 85 | 10.1 | −194 |
| Ex.13 | E 5 | 85 | 9.9 | −195 |
| Ex.14 | E 6 | 88 | 11.1 | −63 |
| Ex.15 | E 7 | 88 | 10.7 | −138 |
| Ex.16 | E 8 | 83 | 10.9 | −148 |
| C.Ex.1 | C B 1 5 | 74 | 7.9 | +193 |
| C.Ex.2 | S 8 1 1 | 73 | 10.1 | +7 |
| C.Ex.3 | C N | 82 | 5.2 | +34 |

Ex.: Example, C.Ex.: Comparative Example

Iso-N* shows a phase transfer temperature from an isotropic phase to a chiral nematic phase.

Example 17

(Formula (1): n=3, A=—Cy—COOH—, X=H, Y=H, B=— (E9)) Preparation of (R)-3-ethyl-1-methylpentyl-4'-(trans-4-n-propylcyclohexylcarbonyloxy)-biphenyl-4-carboxylate
(1) Synthesis of 4'-acetoxybiphenyl-4-carboxylic acid 50 Grams (234 mmol) of 4'-hydroxybiphenyl-4-carboxylic acid and 238 g (2.34 mol) of anhydrous acetic acid were placed in a reactor, and while the mixture was stirred, 0.1 g of concentrated sulfuric acid was added. The stirring was continued until heat generation was terminated, and further, the mixture was stirred under heat at 80° C. for 4 hours. Then, the reaction mixture was gradually cooled to room temperature.

While the reaction mixture was cooled in an ice bath, 500 g of water was gradually added, and the mixture was stirred at room temperature for 3 hours to deactivate unreacted anhydrous acetic acid. A precipitated white solid was recovered by filtration, washed with water to remove acetic acid, and dried with a vacuum dryer, to give 59.8 g of 4'-acetoxybiphenyl-4-carboxylic acid (yield 99%).
(2) Synthesis of 4'-acetoxybiphenyl-4-carbonyl chloride 59.8 Grams (233.4 mmol) of 4'-acetoxybiphenyl-4-carboxylic acid and 278 g (2.33 mol) of purified thionyl chloride were placed in a reactor, and the mixture was refluxed under heat (79° C.) for 4 hours.

Then, thionyl chloride was distilled off under atmospheric pressure, 150 ml of toluene was added, and the toluene and thionyl chloride were distilled off under reduced pressure, to give 63 g of 4'-acetoxybiphenyl-4-carbonyl chloride (yield 98%).
(3) Synthesis of (R)-3-ethyl-1-methylpentyl-4'-acetoxybiphenyl-4-carboxylate 18.6 Grams (67.6 mmol) of 4'-acetoxybiphenyl-4-carbonyl chloride, 8.0 g (61.4 mmol) of (R)-4-ethyl-2-hexanol and 140 ml of toluene were placed in a reactor, 9.7 g (122.9 mmol) of pyridine was dropwise added, and the mixture was stirred at room temperature for 3 hours.

To the reaction solution was added 40 ml of water, the mixture was stirred at room temperature for 30 minutes, and a liquid of an organic layer was separated. The organic layer was washed with 2N hydrochloric acid, with a 1N sodium hydroxide aqueous solution and then with water. The organic layer was dried over anhydrous sodium sulfate and filtered, and the solvent was distilled off, to give 22 g of (R)-3-ethyl-1-methylpentyl-4'-acetoxybiphenyl-4-carboxylate (yield 99%).
(4) Synthesis of (R)-3-ethyl-1-methylpentyl-4'-hydroxybiphenyl-4-carboxylate 22 Grams (59.7 mmol) of (R)-3-ethyl-1-methylpentyl-4'-acetoxybiphenyl-4-carboxylate and 390 ml of toluene were placed in a reactor, 9.3 g of a methanol solution having a methylamine concentration of 40% (119.4 mmol of methylamine) was dropwise added, and the mixture was stirred at room temperature for 3 hours.

The reaction mixture was washed with 2N hydrochloric acid and with water, and a liquid of an organic layer was separated. The organic layer was dried over anhydrous sodium sulfate and filtered, and then the solvent was distilled off, to give 19 g of (R)-3-ethyl-1-methylpentyl-4'-hydroxybiphenyl-4-carboxylate (yield 97%).

(5) Synthesis of (R)-3-ethyl-1-methylpentyl-4'-(trans-4-n-propylcyclohexylcarbonyloxy)-biphenyl-4-carboxylate 0.78 Gram (4.6 mmol) of trans-4-n-propylcyclohexylcarboxylic acid, 0.95 g (4.6 mmol) of N,N-dicyclohexylcarbodiimide (DCC) and 25 ml of dichloromethane were placed in a reactor, and 1.5 g (4.6 mmol) of (R)-3-ethyl-1-methylpentyl-4'-hydroxybiphenyl-4-carboxylate was added. Then, 0.11 g (0.23 mmol) of 4-dimethylaminopyridine was added, and the mixture was stirred at room temperature for 12 hours.

After completion of the reaction, a precipitated solid was separated by filtration and washed with diethyl ether. To the filtrate was added 50 ml of diethyl ether, and the mixture was washed with 2N hydrochloric acid, with a 1N sodium hydroxide aqueous solution and then with water. An organic layer was dried over anhydrous sodium sulfate and filtered, and then the solvent was distilled off to give 2.2 g of crude (R)-3-ethyl-1-methylpentyl-4'-(trans-4-n-propylcyclohexylcarbonyloxy)-biphenyl-4-carboxylate (yield 98%).

The thus-obtained crude product was purified with a liquid chromatograph, to give 1.8 g of (R)-3-ethyl-1-methylpentyl-4'-(trans-4-n-propylcyclohexylcarbonyloxy)-biphenyl-4-carboxylate as an end product (yield 80%).

Example 18
(Formula (1): n=3, A=--, X=H, Y=H, B=--(E10))
Preparation of (R)-3-ethyl-1-methylpentyl-4'-n-propylbiphenyl-4-carboxylate 3.0 Grams (12.5 mmol) of 4'-n-propylbiphenyl-4-carboxylic acid, 2.6 g (12.5 mmol) of N,N-dicyclohexylcarbodiimide (DCC) and 50 ml of dichloromethane were placed in a reactor, 1.6 g (12.5 mmol) of (R)-4-ethyl-2-hexanol was added, then, 0.3 g (2.49 mmol) of 4-dimethylaminopyridine was added, and the mixture was stirred at room temperature for 12 hours.

After completion of the reaction, a precipitated solid was separated by filtration and washed with diethyl ether. To the filtrate was added 100 ml of diethyl ether, and the mixture was washed with 2N hydrochloric acid, with a 1N sodium hydroxide aqueous solution and then with water. An organic layer was dried over anhydrous sodium sulfate and filtered, and then the solvent was distilled off, to give 4.2 g of crude (R)-3-ethyl-1-methylpentyl-4'-n-propylbiphenyl-4-carboxylate (yield 94%).

The thus-obtained crude product was purified with a liquid chromatograph, to give 3.5 g of (R)-3-ethyl-1-methylpentyl-4'-n-propylbiphenyl-4-carboxylate as an end product (yield 79%).

Examples 19–21
(Formula (1): n=3, A=--COO--, X=H, Y=H, B=--(E11)) Preparation of (R)-3-ethyl-1-methylpentyl-4'-n-butanoyloxybiphenyl-4-carboxylate, (Formula (1): n=2, A=--, X=H, Y=H, B=--(E12)) Preparation of (R)-3-ethyl-1-methylpentyl-4'-n-ethylbiphenyl-4-carboxylate, and (Formula (1): n=2, A=--O--, X=H, Y=H, B=--(E13)) Preparation of (R)-3-ethyl-1-methylpentyl-4'-n-ethyloxybiphenyl-4-carboxylate Each Synthesis was carried out in the same manner as in Example 18 except that the 4'-n-propylbiphenyl-4-carboxylic acid was replaced with 4'-n-butanoyloxybiphenyl-4-carboxylic acid, 4'-n-ethylbiphenyl-4-carboxylic acid or 4'-n-ethyloxybiphenyl-4-carboxylic acid.

The optically active compounds (E9 to E13) obtained in the above Examples 17 to 21 were subjected to $^1$H-NMR measurement. Table 5 shows the results from common portions represented by the general formula (I) and left alkyl portions.

Further, the compounds (E9 to E13) were evaluated for phase transition temperatures by observation through a polarizing microscope and DSC measurement. Table 6 shows the results.

TABLE 5

| Compound | Leftmost alkyl chain | | Left and right phenylene groups (biphenylene groups) | | | | | | | | Rightmost alkyl chain | |
| --- | --- | --- | --- | --- | --- | --- | --- | --- | --- | --- | --- | --- |
| | Methyl | Methylene | 1 | 2 | 3 | 4 | 5 | 6 | 7 | 8 | 9 | 10 |
| E9 | 0.88 | *1 | 7.16 | 7.62 | 7.16 | 7.62 | 7.62 | 8.09 | 7.62 | 8.09 | 5.25 | 0.88 |
| E10 | 0.98 | 2.64 | 7.26 | 7.54 | 7.26 | 7.54 | 7.64 | 8.08 | 7.64 | 8.08 | 5.26 | 0.87 |
| E11 | 1.07 | 2.58 | 7.18 | 7.62 | 7.18 | 7.62 | 7.62 | 8.09 | 7.62 | 8.09 | 5.26 | 0.87 |
| E12 | 1.31 | 2.70 | 7.26 | 7.54 | 7.26 | 7.54 | 7.63 | 8.08 | 7.63 | 8.08 | 5.26 | 0.87 |
| E13 | 1.40 | 4.09 | 6.98 | 7.55 | 6.98 | 7.55 | 7.61 | 8.06 | 7.61 | 8.06 | 5.26 | 0.87 |

Note) *1: It is shown that while a peak of a methylene group appeared in the range of 1.0 to 2.0 ppm, no shifted position was specifiable.

TABLE 6

| No. | Compound | Phase sequence |
| --- | --- | --- |
| Ex.17 | E 9 | Iso(111)SA(66)SX(?)Cry |
| Ex.18 | E 10 | Iso(−10)Cry |
| Ex.19 | E 11 | Iso(36)Cry |
| Ex.20 | E 12 | Iso(2)Cry |
| Ex.21 | E 13 | Iso(69)Cry |

Example
Note) Parenthesized values show phase transfer temperatures (° C.), and "(?)" shows that no crystallization took place until a temperature of −50° C. was reached at a temperature decrease ratio of 5° C./minute. Iso stands for an isotropic phase, SA stands for a smectic A phase, SX stands for a smectic phase that was not identified, and Cry stands for a crystal phase.

Examples 22–26

The optically active compounds (E9 to E13) obtained in Examples 17 to 21 were measured to determine a helical twisting power (HTP) and a wavelength shift in the same manner as in Example 9. Concerning the compound E12 alone, 10% by weight of the compound E12 was added to the nematic liquid crystal to prepare a composition, and the composition was measured. Further, since a liquid crystal composition containing the compound E12 and a liquid crystal composition containing the compound E13 did not show any characteristic reflection at 60° C., wavelength shifts (*1) between a wavelength at 25° C. and a wavelength at 50° C. were determined. Table 7 shows the results.

TABLE 7

| No. | Added Compound Name | Iso-N*(° C.) | HTP (1/μm) | Wavelength shift (nm) |
|---|---|---|---|---|
| Ex.22 | E 9 | 86 | 10.5 | −226 |
| Ex.23 | E 1 0 | 64 | 13.9 | −10 |
| Ex.24 | E 1 1 | 69 | 12.9 | −65 |
| Ex.25 | E 1 2 | 72 | 13.8 | −26(*1) |
| Ex.26 | E 1 3 | 69 | 14.4 | −30(*1) |

Notes to Table 7: (*1) shows a wavelength shift between a wavelength at 25° C. and a wavelength at 50° C., the others are wavelength shifts between a wavelength at 25° C. and a wavelength at 60° C., and Iso-N* shows a phase transfer temperature (upper-limit temperature of N* phase) from an isotropic phase to a chiral nematic phase.

Example 27

(Formula (1): n=3, A=—, X=H, Y=H, B=—Ph—COO— (E14)), Preparation of (R)-4-(3-ethyl-1-methylpentyloxycarbonyl)phenyl-4'-n-propylbiphenyl-4-carboxylate 1.5 Grams (6.2 mmol) of 4'-n-propylbiphenyl-4-carboxylic acid, 1.29 g (6.2 mmol) of N,N-dicyclohexylcarbodiimide (DCC) and 30 ml of dichloromethane were placed in a reactor, 1.56 g (6.2 mmol) of (R)-3-ethyl-1-methylpentyl-4-hydroxybenzoate was added, then, 0.15 g (1.2 mmol) of 4-dimethylaminopyridine was added, and the mixture was stirred at room temperature for 12 hours.

After completion of the reaction, a precipitated solid was separated by filtration and washed with diethyl ether. To a filtrate was added 60 ml of diethyl ether, and the mixture was washed with 2N hydrochloric acid, with a 1N sodium hydroxide aqueous solution and then with water. An organic layer was dried over anhydrous sodium sulfate and filtered, and the solvent was distilled off, to give 2.7 g of crude (R)-4-(3-ethyl-1-methylpentyloxycarbonyl)phenyl-4'-n-propylbiphenyl-4-carboxylate (yield 91%).

The thus-obtained crude product was purified with a liquid chromatograph, to give 2.2 g of (R)-4-(3-ethyl-1-methylpentyloxycarbonyl)phenyl-4'-n-propylbiphenyl-4-carboxylate as an end product (yield 74%).

Example 28

(Formula (1): n=3, A=—, X=H, Y=F, B=—Ph—COO— (E15)), Preparation of (R)-3-fluoro-4-(3-ethyl-1-methylpentyloxycarbonyl)phenyl-4'-n-propylbiphenyl-4-carboxylate (R) -3-fluoro-4-(3-ethyl-1-methylpentyloxycarbonyl) phenyl-4'-n-propylbiphenyl-4-carboxylate was synthesized in the same manner as in Example 27 except that the (R)-3-ethyl-1-methylpentyl-4-hydroxybenzoate was replaced with (R)-3-ethyl-1-methylpentyl-2-fluoro-4-hydroxybenzoate.

Example 29

(Formula (1): n=0, A=—, X=H, Y=H, B=—Ph—COO— (E16)), Preparation of (R)-4-(3-ethyl-1-methylpentyloxycarbonyl)phenyl-biphenyl-4-carboxylate (R)-4-(3-ethyl-1-methylpentyloxycarbonyl)phenyl-biphenyl-4-carboxylate was synthesized in the same manner as in Example 27 except that the 4'-n-propylbiphenyl-4-carboxylic acid was replaced with biphenyl-4-carboxylic acid.

Example 30

(Formula (1): n=3, A=—Cy—, X=H, Y=H, B=—COO— (E17)), Preparation of (R)-4-(3-ethyl-1-methylpentyloxycarbonyl)phenyl-4-(trans-4-n-propylcyclohexyl)phenylcarboxylate (1) Synthesis of 4-acetoxybenozic acid chloride 40.0 Grams (222 mmol) of 4-acetoxybenzoic acid and 264 g (2.22 mol) of purified thionyl chloride were placed in a reactor, and the mixture was refluxed under heat (79° C.) for 4 hours.

Then, thionyl chloride was first distilled off under atmospheric pressure, 150 ml of toluene was added, and toluene and thionyl chloride were distilled off under reduced pressure, to give 44 g of 4-acetoxybenzoic acid chloride (yield 99%).

(2) Synthesis of (R)-3-ethyl-1-methylpentyl-4-acetoxybenzoate 10.0 Grams (50.4 mmol) of 4-acetoxybenzoic acid chloride, 6.0 g (46.1 mmol) of (R)-4-ethyl-2-hexanol and 100 ml of toluene were placed in a reactor, 7.3 g (92.1 mmol) of pyridine was dropwise added, and the mixture was stirred at room temperature for 3 hours.

To the reaction solution was added 20 ml of water, the mixture was stirred at room temperature for 30 minutes, and a liquid of an organic layer was separated. The organic layer was washed with 2N hydrochloric acid, with a 1N sodium hydroxide aqueous solution and then with water. The organic layer was dried over anhydrous sodium sulfate and filtered, and then the solvent was distilled off, to give 13.5 g of (R)-3-ethyl-1-methylpentyl-4-acetoxybenzoate (yield 92%).

(3) Synthesis of (R)-3-ethyl-1-methylpentyl-4-hydroxybenzoate 13.5 Grams (46.2 mmol) of (R)-3-ethyl-1-methylpentyl-4-acetoxybenzoate and 230 ml of toluene were placed in a reactor, 7.2 g of a methanol solution having a methylamine concentration of 40% (92.4 mmol of methylamine) was dropwise added, and the mixture was stirred at room temperature for 3 hours.

The reaction solution was washed with 2N hydrochloric acid and with water, and a liquid of an organic layer was separated. The organic layer was dried over anhydrous sodium sulfate and filtered, and then the solvent was distilled off, to give 11 g of (R)-3-ethyl-1-methylpentyl-4-hydroxybenzoate (yield 95%).

(4) Synthesis of (R)-4-(3-ethyl-1-methylpentyloxycarbonyl) phenyl-4-(trans-4-n-propylcyclohexyl)phenylcarboxylate 1.5 Grams (6.1 mmol) of 4-(trans-4-n-propylcyclohexyl) benzoic acid, 1.26 g (6.1 mmol) of N,N-dicyclohexylcarbodiimide (DCC) and 30 ml of dichloromethane were placed in a reactor, 1.52 g (6.1 mmol) of (R)-3-ethyl-1-methylpentyl-4-hydroxybenzoate was added, then, 0.15 g (1.2 mmol) of 4-dimethylaminopyridine was added, and the mixture was stirred at room temperature for 12 hours.

After completion of the reaction, a precipitated solid was separated by filtration and washed with diethyl ether. To a filtrate was added 60 ml of diethyl ether, and the mixture was washed with 2N hydrochloric acid, with a 1N sodium hydroxide aqueous solution and then with water. An organic layer was dried over anhydrous sodium sulfate and filtered, and then, the solvent was distilled off, to give 2.8 g of crude (R)-4-(3-ethyl-1-methylpentyloxycarbonyl)phenyl-4-(trans-4-n-propylcyclohexyl)phenylcarboxylate (yield 96%).

The thus-obtained crude product was purified with a liquid chromatograph, to give 2.4 g of (R)-4-(3-ethyl-1-methylpentyloxycarbonyl)phenyl-4-(trans-4-n-propylcyclohexyl)phenylcarboxylate as an end product (yield 80%).

Example 31

(Formula (1): n=3, A=—Cy—, X=H, Y=F, B=—COO— (E18)), Preparation of (R)-3-fluoro-4-(3-ethyl-1-methylpentyloxycarbonyl)phenyl-4-(trans-4-n-propylcyclohexyl)phenylcarboxylate (R)-3-fluoro-4-(3-ethyl-1-methylpentyloxycarbonyl)phenyl-4-(trans-4-n-propylcyclohexyl)phenylcarboxylate was synthesized in the same manner as in Example 30 except that the 4-acetoxybenzoic acid in Example 30(1) was replaced with 2-fluoro-4-acetoxybenzoic acid.

Example 32

(Formula (1): n=3, A =—O—, X=H, Y=H, B=—COO— (E19)), Preparation of (R)-4-(3-ethyl-1-methylpentyloxycarbonyl)phenyl-4-n-propyloxybenzoate 1.44 Grams (8.0 mmol) of 4-n-propyloxybenzoic acid, 1.65 g (8.0 mmol) of N,N-dicyclohexylcarbodiimide (DCC) and 30 ml of dichloromethane were placed in a reactor, 2.0 g (8.0 mmol) of (R)-3-ethyl-1-methylpentyl-4-hydroxybenzoate was added, then, 0.20 g (1.6 mmol) of 4-dimethylaminopyridine was added, and the mixture was stirred at room temperature for 12 hours.

After completion of the reaction, a precipitated solid was separated by filtration and washed with diethyl ether. To a filtrate was added 60 ml of diethyl ether, and the mixture was washed with 2N hydrochloric acid, with a 1N sodium hydroxide aqueous solution and then with water. An organic layer was dried over anhydrous sodium sulfate and filtered, and the solvent was distilled off, to give 3.2 g of crude (R)-4-(3-ethyl-1-methylpentyloxycarbonyl)phenyl-4-n-propyloxybenzoate (yield 97%).

The thus-obtained crude product was purified with a liquid chromatograph, to give 2.5 g of (R)-4-(3-ethyl-1-methylpentyloxycarbonyl)phenyl-4-n-propyloxybenzoate as an end product (yield 76%).

Example 33

(Formula (1): n=3, A=—COO—, X=H, Y=F, B=—COO— (E20)), Preparation of (R)-3-fluoro-4-(3-ethyl-1-methylpentyloxycarbonyl)phenyl-4-n-butanoyloxybenzoate (R) -3-fluoro-4-(3-ethyl-1-methylpentyloxycarbonyl)phenyl-4-n-butanoyloxybenzoate was synthesized in the same manner as in Example 32 except that the 4-n-propyloxybenzoic acid and the (R)-3-ethyl-1-methylpentyl-4-hydroxybenzoate were replaced with 4-n-butanoyloxybenzoic acid and (R)-3-ethyl-1-methylpentyl-2-fluoro-4-hydroxybenzoate, respectively.

The optically active compounds (E14 to E20) obtained in the above Examples 27 to 33 were subjected to $^1$H-NMR measurement. Table 8 shows the results from common portions represented by the general formula (I), and Table 9 shows the results from portions specific to the compounds.

Further, the compounds (E14 to E20) were evaluated for phase transition temperatures by observation through a polarizing microscope and DSC measurement. Table 10 shows the results.

TABLE 8

| Compound | Left phenylene group | | | | Right phenylene group | | | | Rightmost alkyl chain | |
|---|---|---|---|---|---|---|---|---|---|---|
| | 1 | 2 | 3 | 4 | 5 | 6 | 7 | 8 | 9 | 10 |
| E14 | 7.73 | 8.25 | 7.73 | 8.25 | 7.32 | 8.13 | 7.32 | 8.13 | 5.25 | 0.87 |
| E15 | 7.73 | 8.23 | 7.73 | 8.23 | 7.12 | — | 7.12 | 8.02 | 5.27 | 0.87 |
| E16 | 7.75 | 8.25 | 7.75 | 8.25 | 7.12 | — | 7.12 | 8.02 | 5.27 | 0.87 |
| E17 | 7.35 | 8.11 | 7.35 | 8.11 | 7.27 | 8.11 | 7.27 | 8.11 | 5.24 | 0.89 |
| E18 | 7.36 | 8.09 | 7.36 | 8.09 | 7.08 | — | 7.08 | 8.00 | 5.26 | 0.89 |
| E19 | 6.98 | 8.13 | 6.98 | 8.13 | 7.28 | 8.13 | 7.28 | 8.13 | 5.25 | 0.87 |
| E20 | 7.28 | 8.26 | 7.28 | 8.26 | 7.11 | — | 7.11 | 8.00 | 5.28 | 0.92 |

TABLE 9

| Compound | Leftmost alkyl chain | | B portion | | | | |
|---|---|---|---|---|---|---|---|
| | Methyl | Methylene | Structural formula | Benzene ring portion | | | |
| E14 | 0.99 | 2.66 | —Ph—COO— | 7.32 | 7.58 | 7.32 | 7.58 |
| E15 | 1.00 | 2.65 | —Ph—COO— | 7.28 | 7.58 | 7.28 | 7.58 |
| E16 | — | — | —Ph—COO— | 7.50 | 7.66 | 7.50 | 7.66 |
| E17 | 0.89 | *1 | —COO— | — | — | — | — |
| E18 | 0.89 | *1 | —COO— | — | — | — | — |
| E19 | 1.07 | 4.02 | —COO— | — | — | — | — |
| E20 | 1.10 | 2.63 | —COO— | — | — | — | — |

Note) *1 shows that a peak of a methylene group appeared at 1 to 2 ppm but that no corresponding shift portion was specifiable.

TABLE 10

| No. | Compound | Phase sequence |
|---|---|---|
| Ex.27 | E 1 4 | Iso(125)SA(96)Cry |
| Ex.28 | E 1 5 | Iso(113)SA(75)Cry |
| Ex.29 | E 1 6 | Iso(48)Cry |
| Ex.30 | E 1 7 | Iso(77)SA(45)Cry |
| Ex.31 | E 1 8 | Iso(65)SA(56)Cry |
| Ex.32 | E 1 9 | Iso(51)Cry |
| Ex.33 | E 2 0 | Iso(35)Cry |

Ex.: Example
Notes) Parenthesized values show phase transfer temperatures (° C.), Iso stands for an isotropic phase, SA stands for a smectic A phase, and Cry stands for a crystal phase.
Examples 34–40

The optically active compounds obtained in Examples 27 to 33 (E14 to E20) were measured to determine helical twisting powers (HTP) and wavelength shifts in the same manner as in Example 9. Table 11 shows the results.

TABLE 11

| No. | Added Compound Name | Iso-N*(° C.) | HTP (1/µm) | Wavelength shift (nm) |
|---|---|---|---|---|
| Ex.34 | E 1 4 | 85 | 10.5 | −185 |
| Ex.35 | E 1 5 | 83 | 9.5 | −145 |
| Ex.36 | E 1 6 | 76 | 11.0 | −75 |
| Ex.37 | E 1 7 | 83 | 11.3 | −74 |
| Ex.38 | E 1 8 | 82 | 10.5 | −78 |

TABLE 11-continued

| No. | Added Compound Name | Iso-N*(° C.) | HTP (1/μm) | Wavelength shift (nm) |
|---|---|---|---|---|
| Ex.39 | E 1 9 | 69 | 13.0 | −32 |
| Ex.40 | E 2 0 | 70 | 10.7 | −19 |

Ex.: Example
Note) Iso-N* shows a phase transfer temperature (upper-limit temperature of N* phase) from an isotropic phase to a chiral nematic phase.

Examples 41–46

To a nematic liquid crystal (ZLI-4718) supplied by Merck & Co., Inc., was added 15% by weight of the optically active compound (E1, E9, E11, E14, E17 or E19) obtained in Example 1, 17, 20, 27, 30 or 32, to prepare chiral nematic (N*) liquid crystal compositions. The thus-prepared compositions were measured to determine helical twisting powers (HTP) and wavelength shifts in the same manner as in Example 9. As a refractive index n, there was employed a value of 1.6 which the base liquid crystal ZLI-4718 had. Table 12 shows the results. The above optically active compounds also showed great HTPs and great minus wavelength shifts even when added to the nematic liquid crystal (ZLI-4718).

TABLE 12

| No. | Added Compound Name | Iso-N*(° C.) | HTP (1/μm) | Wavelength shift (nm) |
|---|---|---|---|---|
| Ex.41 | E 1 | 90 | 12 | −159 |
| Ex.42 | E 9 | 92 | 13 | −94 |
| Ex.43 | E 1 1 | 73 | 15 | −44 |
| Ex.44 | E 1 4 | 90 | 12 | −96 |
| Ex.45 | E 1 7 | 88 | 13 | −62 |
| Ex.46 | E 1 9 | 74 | 15 | −38 |

Ex.: Example
Note) Iso-N* shows a phase transfer temperature (upper-limit temperature of N* phase) from an isotropic phase to a chiral nematic phase.

What is claimed is:

1. An optically active compound of the following general formula (1), (1)

wherein n is an integer of 0 to 5, provided that when n is 0, A is a single bond (—) and that when n is 1 to 5, A is a single bond (—), —O—, —COO—, —Cy— or —Cy—COO— in which —Cy— is a trans-1,4-cyclohexylene group, each of X and Y is independently a hydrogen atom or a fluorine atom, B is a single bond (—), —COO—, —COO—Ph— or —Ph—COO— in which —Ph— is a 1,4-phenylene group, and C* is an asymmetric carbon.

2. The optically active compound of claim 1, wherein n in the general formula (1) is 3.

3. The optically active compound of claim 1, wherein X and Y in the general formula (1) are hydrogen atoms.

4. The optically active compound of claim 1, which has the general formula (1) wherein A is a single bond (—) and B is —COO—Ph— or —Ph—COO—.

5. The optically active compound of claim 1, which has the general formula (1) wherein n is 3, X and Y are hydrogen atoms, A is a single bond (—) and B is —COO—Ph— or —Ph—COO—.

6. The optically active compound of claim 1, which has the general formula (1) wherein B is a single bond (—) and A is a single bond (—), —O—, —COO— or —Cy—COO—.

7. The optically active compound of claim 1, which has the general formula (1) wherein n is 3, X and Y are hydrogen atoms, A is —Cy—COO— and B is a single bond (—).

8. The optically active compound of claim 1, which has the general formula (1) wherein B is —COO— and A is —O—, —COO— or —Cy—.

9. The optically active compound of claim 1, which has a helical twisting power (HTP) of at least 9.

10. The optically active compound of claim 1, which has an induced helical pitch that decreases in length with an increase in temperature.

* * * * *